United States Patent [19]
Kobylinski et al.

[11] Patent Number: 4,729,981
[45] Date of Patent: Mar. 8, 1988

[54] ROR-ACTIVATED CATALYST FOR SYNTHESIS GAS CONVERSION

[75] Inventors: Thaddeus P. Kobylinski, Vero Beach, Fla.; Charles L. Kibby, Gibsonia, Pa.; Richard B. Pannell, Allison Park, Pa.; Elizabeth L. Eddy, Gibsonia, Pa.

[73] Assignee: Shell Internationale Research Maatschappij B.V., The Hague, Netherlands

[21] Appl. No.: 869,705

[22] Filed: Jun. 2, 1986

Related U.S. Application Data

[60] Division of Ser. No. 734,189, May 15, 1985, Pat. No. 4,605,676, which is a continuation-in-part of Ser. No. 635,911, Jul. 30, 1984, Pat. No. 4,585,798, which is a continuation-in-part of Ser. No. 310,969, Oct. 13, 1981, abandoned, and a continuation-in-part of Ser. No. 540,662, Oct. 11, 1983, Pat. No. 4,493,905, which is a division of Ser. No. 310,977, Oct. 13, 1981, Pat. No. 4,413,064.

[51] Int. Cl.⁴ .............................................. B01J 23/70
[52] U.S. Cl. .................................. 502/259; 502/260; 502/325; 502/335; 502/337; 518/715
[58] Field of Search ............... 502/259, 260, 325, 337, 502/335

[56] References Cited

U.S. PATENT DOCUMENTS

| | | | |
|---|---|---|---|
| 4,002,658 | 6/1977 | Della Betta et al. | 502/337 |
| 4,026,823 | 5/1977 | Van Hook et al. | 502/337 |
| 4,090,980 | 5/1978 | Carter et al. | 502/259 |
| 4,413,064 | 11/1983 | Beuther et al. | 518/715 |
| 4,493,905 | 1/1985 | Beuther et al. | 502/201 |
| 4,585,798 | 4/1986 | Beuther et al. | 518/715 |
| 4,605,676 | 8/1986 | Kobylinski et al. | 518/700 |

FOREIGN PATENT DOCUMENTS 796921  6/1958  United Kingdom ............... 502/337

*Primary Examiner*—Asok Pal
*Attorney, Agent, or Firm*—Roylance, Abrams, Berdo & Goodman

[57] ABSTRACT

Catalyst for synthesis gas conversion in which a gas comprising carbon monoxide and hydrogen is converted to a liquid hydrocarbon is prepared by subjecting cobalt or nickel on a refractory metal oxide support to an activation procedure at a temperature of from about 100° to about 450° C. comprising, in sequence, (A) reduction in hydrogen, (B) oxidation in an oxygen-containing gas, and (C) reduction in hydrogen.

38 Claims, No Drawings

ROR-ACTIVATED CATALYST FOR SYNTHESIS GAS CONVERSION

CROSS-REFERENCE TO RELATED APPLICATIONS

This application is a continuation-in-part of U.S. Ser. No. 635,911 filed July 30, 1984, now U.S. Pat. No. 4,585,798 which, in turn, is a continuation-in-part of U.S. Ser. No. 310,969 filed Oct. 13, 1981 now abandoned and U.S. Ser. No. 540,662 filed Oct. 11, 1983, now U.S. Pat. No. 493,905 which, in turn, is a divisional of U.S. Ser. No. 310,977 filed Oct. 13, 1981, now U.S. Pat. No. 4,413,064, all in the name of H. Beuther et al.

FIELD OF THE INVENTION

The present invention relates to a process for the conversion of synthesis gas to liquid hydrocarbons in the presence of a supported cobalt or nickel catalyst, to the preparation of such catalyst and to the catalyst, per se. More particularly, this invention relates to conversion of synthesis gas to liquid hydrocarbons using cobalt or nickel on a refractory metal oxide support as catalyst that has been subjected to an activation treatment to provide improved activity and selectivity.

BACKGROUND INFORMATION

The growing importance of alternative energy sources has brought a renewed interest in the Fischer-Tropsch synthesis as one of the more attractive direct and environmentally acceptable paths to high quality transportation fuels. The Fischer-Tropsch synthesis involves the production of hydrocarbons by the catalyzed reaction of CO and hydrogen. Commercial plants have operated in Germany, South Africa and other parts of the world based on the use of particular catalysts.

The use of promoted cobalt catalysts has attracted wide attention. For example, the German commercial operation concentrated on the use of a precipitated cobalt-thoria-kieselguhr fixed-bed catalyst, and a later modification in which MgO, for economy reasons, replaced part of the thoria.

More recently, U.S. Pat. No. 4,088,671 to T. P. Kobylinski describes the use of a ruthenium-promoted cobalt catalyst on a support, such as alumina or kieselguhr, in the synthesis of hydrocarbons from the reaction of CO and hydrogen at substantially atmospheric pressure. As ruthenium is expensive, the patent indicates that it is preferred to employ ruthenium in the minimum amount necessary to achieve the desired result.

Attempts have been made to utilize unpromoted cobalt catalysts for the synthesis of hydrocarbons from synthesis gas. However, unpromoted cobalt often had poor selectivity and requires high metal loadings to provide desirable activity.

SUMMARY OF THE INVENTION

It has now been found in accordance with the present invention, that synthesis gas comprising hydrogen and carbon monoxide can be selectively converted under synthesis gas conversion conditions to liquid hydrocarbons with a catalyst prepared by subjecting a supported cobalt or nickel catalyst to an activation procedure comprising the steps, in sequence, of (A) reduction in hydrogen, (B) oxidation in an oxygen-containing gas, and (C) reduction in hydrogen, the activation procedure being conducted at a temperature below 500° C.

Surprisingly, it has been found that the activation procedure of the present invention provides both promoted and unpromoted, supported cobalt and nickel catalysts with improved reaction rates regardless of whether the catalyst is prepared by impregnation of a support with cobalt or nickel, or by precipitation of cobalt or nickel onto the support. Moreover, the activation procedure of the present invention can significantly improve activity of promoted, supported cobalt and nickel catalysts, wherein promoter, such as ruthenium and lanthana have been previously added to improve activity. The catalyst of the present invention is produced by subjecting a supported cobalt or nickel catalyst to an activation procedure including the steps of (i) reduction, (ii) oxidation, and (iii) reduction, herein termed "ROR activation" while under a temperature below 500° C., preferably below 450° C. As will be hereinafter demonstrated, by subjecting the supported cobalt or nickel catalyst to ROR activation, the activity of the resultant catalyst can be increased by as much as about 100 percent using the activation procedure of the present invention.

The expression "supported cobalt catalyst" or "supported nickel catalyst" as used in the present application means catalyst wherein the cobalt or nickel precursor is deposited on a refractory metal oxide support by means of impregnation or precipitation to distribute the cobalt or nickel metal as small crystallites upon the support. This is contrasted with a catalyst such as the cobalt-substituted layered aluminosilicate described in U.S. Pat. No. 4,492,774 to C. L. Kibby and T. P. Kobylinski in which the cobalt is ionically bonded within the crystal framework of the compound.

According to one embodiment of the present invention, the supported cobalt or nickel catalyst of the present invention is prepared using a non-aqueous, organic solvent impregnation solution for depositing cobalt or nickel onto the support.

According to still another embodiment of the present invention, the cobalt or nickel is precipitated onto the support.

DESCRIPTION OF THE PREFERRED EMBODIMENTS

The supported cobalt and nickel catalysts of the present invention are prepared by any suitable procedure, whether precipitation of the cobalt or nickel onto a refractory oxide support or impregnation of a refractory oxide support using an aqueous or non-aqueous impregnation solution of the nickel or cobalt.

The catalyst can contain from about 1 to about 30 weight percent cobalt based upon total catalyst weight, preferably from about 3 to about 20 weight percent cobalt, with from about 5 to about 15 weight percent cobalt being especially preferred. If nickel is the metal of choice, the catalyst can contain from about 1 to about 50 weight percent nickel based upon total catalyst weight, preferably from about 3 to about 35 weight percent nickel, with from about 10 to about 20 weight percent nickel being especially preferred.

The refractory metal oxide support can be alumina or silica. Alumina is preferred, and the alumina is preferably a gamma or eta alumina. Likewise, extruded gamma or eta alumina can be used. The support of the present invention is characterized as having low acidity, a high surface area and high purity. The expression "low acidity" as used in the present application means that the support has a Bronsted activity with $H_o$ 1.5 which is less than 5 micromol per gram or about $10^{16}$ acid sites per square meter of surface area. The low acidity of the support is required in order to enable the catalyst to provide a higher molecular weight hydrocarbon product.

The surface area of the support of the present invention is at least 40 or 50 square meters per gram but is not so great as to become unduly microporous so as to permit reactant materials to enter the interstices of the catalyst. A suitable surface area is from about 40 to about 250, preferably from about 150 to about 225 square meters per gram.

As indicated, the catalyst support of the present invention should be of high purity. When the catalyst support is alumina, the expression "high purity" means that the catalyst contains negligible amounts of sulfur, silicon, phosphorous or other material having a deleterious effect on the metal dispersion or the production of high molecular weight hydrocarbon products. When a silica support is used, the expression "high purity" means that the catalyst contains negligible amounts of sulfur, aluminum, phosphorous or other material having a deleterious effect on the metal dispersion or the production of high molecular weight hydrocarbon products. For sulfur, the impurity levels should be below 0.1 weight percent, preferably below 0.02 weight percent, and especially below 0.01 weight percent. For impurities creating acid sites, less than 5 micromol per gram should be present (about 0.01–0.1 weight percent depending on molecular weight). The deleterious effect of acidity is isomerization and cracking of intermediate olefins, removing them from chain growth and producing a low molecular weight product.

A promoter, such as ruthenium or the like may be included in the catalyst of the present invention if desired. The amount of ruthenium can be from about 0.01 to about 0.50 weight percent, preferably from about 0.05 to about 0.25 weight percent based upon total catalyst weight.

In accordance with a further embodiment of the present invention, the catalyst of the present invention may additionally contain from about 0.1 to 5 weight percent, preferably from about 0.1 to about 2 weight percent of a suitable promoter metal oxide, such as $La_2O_3$, $MnO_2$, or a Group IIIB or IVB metal oxide. Oxides of the lanthanides and actinides are preferred, and, thus, suitable metal oxides include, for example, $Sc_2O_3$, $Y_2O_3$, $Ac_2O_3$, $Pr_2O_3$, $PrO_2$, $Nd_2O_3$, $Sm_2O_3$, $Eu_2O_3$, $Gd_2O_3$, $Tb_2O_3$, $Tb_4O_7$, $Dy_2O_3$, $Ho_2O_3$, $Er_2O_3$, $Tm_2O_3$, $Yb_2O_3$, $Lu_2O_3$, $UO_2$, $UO_3$, $U_3O_8$, and the like. Especially preferred metal oxides for inclusion in the catalyst of the present invention include $La_2O_3$, $CeO_2$, $ZrO_2$, $TiO_2$, $HfO_2$, $ThO_2$, and unseparated rare earth oxide mixtures high in lanthanum, praseodymium, and neodymium. Additional preferred promoters are $MgO$ and $MnO_2$.

The ROR activation procedure of the present invention may be used to improve activity of the supported catalyst of the present invention regardless of the method used to deposit the catalytic metals on the support. Thus, any technique well known to those having ordinary skill in the art to distend the catalytic metals in a uniform this layer on the catalyst support is suitable here. For example, the cobalt or nickel can be deposited onto the support material by the technique of minimum excess solution from an aqueous solution of a suitable cobalt or nickel, such as the nitrates, chlorides, or acetates; or the cobalt or nickel can be precipitated from an aqueous solution onto a support by techniques well known in the art. The precipitation technique is illustrated in U.S. Pat. No. 4,088,671 to Kolbylinski, the disclosure of which is hereby incorporated by reference.

A preferred method employed to deposit the catalytic metals of the present invention onto the support involves an impregnation technique using non-aqueous, organic impregnation solutions of soluble cobalt or nickel salt and, if desired, a soluble promoter metal salt, e.g., ruthenium salt and lanthanum salt, in order to achieve the necessary metal loading and distribution required to provide a highly selective and active catalyst.

Initially, the support, such as alumina, can be treated by oxidative calcination of the gamma and/or eta-alumina at a temperature in the range of from about 450° to about 900° C., preferably from about 600° to about 750° C. to remove water from the micropores of the support.

Meanwhile, non-aqueous organic solvent solution of a cobalt or nickel salt, and, if desired, non-aqueous organic solvent solutions of ruthenium, lanthanum, and/or manganese salts, for example, are prepared. Any suitable ruthenium salt, such as ruthenium nitrate, chloride, acetate or the like can be used. In addition, any suitable promoter metal, e.g., lanthanum salt, such as lanthanum nitrate or lanthanum acetate or manganese salt, such as manganese nitrate, or the like can be employed. In general, any metal salt which is soluble in the organic solvent of the present invention and will not introduce acidity or have a poisonous effect on the catalyst can be utilized.

The non-aqueous organic solvent is a non-acidic liquid which is formed from moieties selected from the group consisting of carbon, oxygen, hydrogen and nitrogen, and possesses a relative volatility of at least 0.1. The expression "relative volatility" as used in the present application is defined as the ratio of the vapor pressure of the solvent to the vapor pressure of acetone, as reference, when measured at 25° C.

Suitable solvents include, for example, ketones, such as acetone, butanone (methyl ethyl ketone); the lower alcohols, e.g., methanol, ethanol, propanol and the like; amides, such as dimethyl formamide; amines, such as butylamine; ethers, such as diethylether and tetrahydrofuran; hydrocarbons, such as pentane and hexane; and mixtures of the foregoing solvents. The preferred solvents of the present invention are acetone, for cobalt nitrate or tetrahydrofuran.

The amount of solvent utilized is an amount that is at least equivalent to the pore volume of the alumina utilized, but not greater than five times the alumina pore volume. For example, a commercially available gamma-alumina useful in the present invention has a pore volume of between about 0.2 to about 0.7 cubic centimeters pore volume per gram of alumina.

Suitable cobalt salts include, for example, cobalt nitrate, cobalt acetate, cobalt carbonyl, cobalt acetylacetonate, or the like. Suitable nickel salts include nickel nitrate, nickel acetate, nickel carbonyl, nickel acetylacetonate, or the like. Likewise, any suitable ruthenium salt, such as ruthenium nitrate, chloride, acetate or the like can be used. Ruthenium acetylacetonate is preferred. In addition, any suitable promoter metal, e.g., lanthanum salt, such as lanthanum nitrate, lanthanum acetate or the like can be employed. In general, any metal salt which is soluble in the organic solvent of the present invention and will not introduce acidity or have a poisonous effect on the catalyst can be utilized.

The calcined alumina support is then impregnated in a dehydrated state with the non-aqueous, organic solvent solution of the metal salts. Thus, the calcined alumina should not be unduly exposed to atmospheric humidity so as to become rehydrated.

Any suitable impregnation technique can be employed including techniques well known to those skilled in the art so as to distend the catalytic metals in a uniform thin layer on the catalyst support. For example, the cobalt or nickel along with the oxide promoter can be deposited on the support material by the "incipient wetness" technique. Such technique is well known and requires that the volume of impregnating solution be predetermined so as to provide the minimum volume which will just wet the entire surface of the support, with no excess liquid. Alternatively, the excess solution technique can be utilized if desired. If the excess solution technique is utilized, then the excess solvent present, e.g., acetone, is merely removed by evaporation. Thus, the impregnation solution can be added in excess, namely, up to five times the pore volume of the alumina, or can be added using just enough solution to fill the pore volume of the alumina.

Next, the impregnation solution and alumina are stirred while evaporating the solvent at a temperature of from about 25° to about 50° C. until "dryness".

The impregnated catalyst is slowly dried at a temperature of from about 110° to about 120° C. for a period of about 1 hour so as to spread the metals over the entire support. The drying step is conducted at a very slow rate in air.

The dried catalyst may be reduced directly in hydrogen or it may be calcined first. In the case of impregnation with cobalt nitrate, direct reduction can yield a higher cobalt metal dispersion and synthesis activity, but reduction of nitrates is difficult to control and calcination before reduction is safer for large scale preparations. Also, a single calcination step to decompose nitrates is simpler if multiple impgregnations are needed to provide the desired metal loading. Reduction in hydrogen requires a prior purge with inert gas, a subsequent purge with inert gas and a passivation step in addition to the reduction itself, as described later as part of the ROR activation. However, impregnation of cobalt carbonyl must be carried out in a dry, oxygen-free atmosphere and it must be reduced directly, then possivated, if the benefits of its lower oxidation state are to be maintained.

The dried catalyst is calcined by heating slowly in flowing air, for example 10 cc/gram/minute, to a temperature in the range of from about 200° to about 400° C., preferably from about 250° to about 300° C., that is sufficient to decompose the metal salts and fix the metals. The aforesaid drying and calcination steps can be done separately or can be combined. However, calcination should be conducted by using a slow heating rate of, for example, 0.5° to about 3° C. per minute, preferably from about 0.5° to about 1° C. per minute and the catalyst should be held at the maximum temperature for a period of about 1 to about 20 hours, preferably for about 2 hours.

The foregoing impregnation steps are repeated with additional impregnation solutions in order to obtain the desired metal loading. Ruthenium and other promoter metal oxides are conveniently added together with cobalt or nickel, but they may be added in other impregnation steps, separately or in combination, either before, after, or between impregnations of cobalt or nickel.

After the last impregnation sequence, the loaded catalyst support is then subjected to the ROR activation treatment of the present invention. The ROR activation treatment of the present invention must be conducted at a temperature below 500° C. in order to achieve the desired increase in activity and selectivity of the cobalt- or nickel-impregnated catalyst. Temperatures of 500° C. or above reduce liquid hydrocarbon selectivity of the cobalt- or nickel-impregnated catalyst. Suitable ROR activation temperatures are below 500° C., preferably below 450° C., and below 400° C. is especially preferred. Thus, ranges of 100° or 150° to 450° C., preferably 250° to 400° C. are suitable for reduction and oxidation steps. The activation steps are conducted while heating at a rate of from about 0.1° to about 5° C., preferably from about 0.1° to about 2° C.

The impregnated catalyst is preferably slowly reduced in the presence of hydrogen. If the catalyst has been calcined after each impregnation, to decompose nitrates or other salts, then the reduction may be performed in one step with heating in a single temperature ramp (e.g., 1° C./min.) to the maximum temperature and held at that temperature, from about 250° or 300° to about 450° C., preferably from about 350° to about 400° C., for a hold time of 6 to about 65 hours, preferably from about 16 to about 24 hours. If nitrates are still present, the reduction is best conducted in two steps wherein the first reduction heating step is carried out at a slow heating rate of no more than about 5° C. per minute, preferably from about 0.1° to about 1° C. per minute up to a maximum hold temperature of 200° to about 300° C., preferably 200° to about 250° C., for a hold time of from about 6 to about 24 hours, preferably from about 16 to about 24 hours under ambient pressure conditions. In the second reduction heating step, the catalyst can be heated at from about 0.5° to about 3° C. per minute, preferably from about 0.1° to about 1° C. per minute to a maximum hold temperature of from about 250° or 300° up to about 450° C., preferably from about 350° to about 400° C. for a hold time of 6 to about 65 hours, preferably from about 16 to about 24 hours. Although pure hydrogen can be employed for these reduction steps, a mixture of hydrogen and nitrogen can be utilized in order to slowly reduce the catalyst. For example, the reduction can be conducted initially using a gaseous mixture comprising 5% hydrogen and 95% nitrogen, and thereafter, the concentration of hydrogen can be gradually increased until pure hydrogen is obtained so as to slowly reduce the catalyst. Such slow reduction is particularly desirable when the metal salts utilized in the impregnation step are nitrates so as to avoid the dangers involved with an exothermic reaction in which nitrates are reduced.

Thus, the slow reduction may involve the use of a mixture of hydrogen and nitrogen at 100° C. for about one hour; increasing the temperature 0.5° C. per minute until a temperature of 200° C.; holding that temperature for approximately 30 minutes; and then increasing the temperature 1° C. per minute until a temperature of 350° C. is reached and then continuing the reduction for approximately 16 hours. Reduction should be conducted slowly enough and the flow of the reducing gas maintained high enough to maintain the partial pressure of water in the offgas below 1 percent, so as to avoid excessive steaming of the exit end of the catalyst bed.

Before and after all reductions, the catalyst must be purged in an inert gas such as nitrogen, argon or helium.

The reduced catalyst is passivated at ambient temperature (25°–35° C.) by flowing diluted air over the catalyst slowly enough so that a controlled exotherm passes through the catalyst bed. After passivation, the catalyst is heated slowly in diluted air to a temperature of from about 300° to about 350° C. in the same manner as previously described in connection with calcination of the catalyst.

Next, the oxidized catalyst is then slowly reduced in the presence of hydrogen in the same manner as previously described in connection with reduction of the impregnated catalyst. Since nitrates are no longer present, this reduction may be accomplished in a single temperature ramp and held, as described above for reduction of calcined catalysts.

The composite catalyst of the present invention has an average particle diameter, which depends upon the type of reactor to be utilized, of from about 0.01 to about 6 millimeters; preferably from about 1 to about 6 millimeters for a fixed bed; and preferably from about 0.01 to about 0.11 millimeters being preferred for a reactor with the catalyst suspended by gas, liquid, or gas-liquid media (e.g., fluidized beds, slurries, or ebullating beds).

The charge stock used in the process of this invention is a mixture of CO and hydrogen. Any suitable source of the CO and hydrogen can be used. The charge stock can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of this invention, but it may be present as a diluent gas. Sulfur compounds in any form are deleterious to the life of the catalyst and should be removed from the CO—$H_2$ mixture and from any diluent gases.

The reaction temperature is suitably from about 160° to about 350° C., preferably from about 175° to about 275° C., and most preferably from about 185° to about 250° C. The total pressure is, for example, from about 1 to about 100 atmospheres, preferably from about 3 to about 35 atmospheres, and most preferably from about 10 to about 20 atmospheres. Surprisingly, it has been found that the use of pressures of at least 50 psi (3.4 atmospheres) using the low ruthenium catalysts of the present invention results in activities greater than that achievable with larger quantities of ruthenium at the same pressure.

The gaseous hourly space velocity based upon the total amount of feed is less than 20,000 volumes of gas per volume of catalyst per hour, preferably from about 100 to about 5000 v/v/hour, with from about 1000 to about 2500 v/v/hour being especially preferred. If desired, pure synthesis gas can be employed or, alternatively, an inert diluent, such as nitrogen, $CO_2$, methane, steam or the like can be added. As used herein, the expression "inert diluent" indicates that the diluent is non-reactive under the reaction conditions herein disclosed or is a normal reaction product.

The synthesis gas reaction using the catalysts of this invention can occur in a fixed, fluid or moving bed type of operation.

The invention will be further described with reference to the following experimental work.

EXAMPLE 1

A catalyst (denoted "catalyst A") was prepared by impregnating 22.002 grams of a gamma-alumina (Ketjen EC commercially availably from Akzo Chemie) with 8.700 grams of dicobalt octacarbonyl in tetrahydrofuran in an oxygen-free atmosphere. The alumina was treated with acetone and calcined at 300° C. prior to impregnation. The catalyst was loaded into a reactor in a glovebox. Initially, the catalyst was activated by heating at 5° C. per minute in 1680 cubic centimeters per gram per hour of hydrogen to a temperature of 185° C. at which temperature the catalyst was held for one hour. The reduced weight of the catalyst was 12 weight percent cobalt and 88 weight percent alumina.

The catalyst was subjected to a synthesis run in which the catalyst was contacted with hydrogen and carbon monoxide at a ratio of 1.85 at a temperature of 195° C. under a pressure of one bar at a synthesis gas flow rate of 1680 cubic centimeters per gram of catalyst per hour. Thereafter, the catalyst was purged in hydrogen at 185° C., and then heated at a rate of 1° C. per minute to a temperature of 350° C. and held at such temperature for a period of one hour (treatment to this point denoted "R350"). The catalyst was then subjected to synthesis at 195° C., under the conditions previously indicated, and then purged in hydrogen, and cooled in nitrogen to room temperature. While under room temperature conditions, the catalyst was dosed with 6 pulses of an air/nitrogen mixture. Next, oxidation of the catalyst was conducted in flowing air by heating at a temperature of 1° C. per minute until the catalyst reached 300° C. where it was held for a period of five and one-half hours. The catalyst was then purged in nitrogen and cooled. Finally, the catalyst was reduced once again by heating at a rate of 1° C. per minute in hydrogen until a temperature of 350° C. was reached and then holding at that temperature for five and one-half hours (treatment to this point denoted "ROR").

For comparative purposes, a catalyst containing 20 weight percent cobalt, 0.5 weight percent ruthenium and 1.0 weight percent $La_2O_3$ (catalyst B) prepared by impregnating gamma-alumina (Ketjen-CK-300) with cobalt nitrate rather than cobalt carbonyl, was tested under the identical conditions of the aforesaid cobalt carbonyl catalyst (catalyst A).

The results of the foregoing tests made at 195° C. and a hydrogen to carbon monoxide ratio of 1.5 are set forth in Table I:

TABLE I

| Catalyst | CO Conversion Rate (cc/gram metal/hour) | |
|---|---|---|
|  | R350 | ROR |
| A | 1506 | 1726 |
| B | 1034 | 1415 |

The results set forth in Table I demonstrate that the ROR treatment produces catalysts having higher activity than catalysts without ROR. The ROR activation increased the activity of Catalyst A by 15 percent, and increased Catalyst B by 37 percent.

EXAMPLE 2

This example demonstrates the ROR activation on a catalyst after incorporating a promoter into the cobalt catalyst.

Ruthenium-promoted cobalt carbonyl catalyst samples were prepared by impregnating an alumina support identical to that used in Example 1 with lanthanum nitrate in acetone. The impregnated support was dried to remove the solvent and then calcined for two hours at a temperature of 300° C. Next, ruthenium acetylacetonate in acetone was added and the catalyst reduced in hydrogen while being heated at a rate of 2° C. per minute until a temperature of 200° C. was reached. The catalyst was then maintained at 200° C. for two hours. This catalyst is denoted "Catalyst C". Additional catalyst samples (denoted "Catalyst D") were prepared in a manner identical to Catalyst C except that the lanthanum nitrate addition step was omitted.

After reduction, the resulting catalyst sample was impregnated with dicobalt octacarbonyl in tetrahydrofuran, without exposure to air, and was stored in a controlled atmosphere glove-box. The catalyst was prepared to contain 12 weight percent cobalt and 0.3 weight percent ruthenium in the reduced state.

Next, hydrogen sorption measurements were performed in a static volumetric apparatus, and for each test, 2 gram samples were placed in chemisorption cells inside the glove-box and the cells were then sealed and transferred to the sorption unit. The catalysts were evacuated, then reduced in hydrogen as they were heated to 350° C. and held at that temperature for one hour. After evacuation at 350° C., the samples were cooled to room temperature for hydrogen sorption measurements. The sorption capacities at 100-500 torr were measured and the total sorption capacity was estimated by extrapolation to zero pressure.

The catalysts were then reduced again at 350° C. for one hour and hydrogen sorption capacities were again measured. For one sample, the 185° C. reduction was omitted and a reduction overnight at 350° C. was performed instead. It was found that there was little difference between 185° C. and 350° C. reductions. Following the 350° C. reduction, the hydrogen corption capacities were again measured. Then the catalysts were passivated by dosing in air three times to 500 torr and they were then oxidized in flowing air while heating to 300° C. at a rate of 1° C. per minute and were held at that temperature for a period of five and one-half hours. Finally, they were again reduced overnight at 350° C. and their hydrogen sorption capacities were again measured.

The results of the hydrogen sorption and metal dispersion tests are set forth below in Table II:

TABLE II

| Catalysts | R350 | ROR |
|---|---|---|
| | Hydrogen Sorption Capacity (millimoles/gram) | |
| A | 0.241 | 0.112 |
| C | 0.234 | 0.190 |
| D | 0.231 | 0.169 |
| | Metal Dispersion H/(Co + Ru) | |
| A | 0.29 | 0.13 |
| C | 0.27 | 0.22 |
| D | 0.27 | 0.20 |

Measurements of hydrogen sorption capacities on the catalysts made with dicobalt octacarbonyl showed that their metal dispersions were about 30 percent after mild reduction. That is about 1.5-2.0 times higher than dispersions obtained by impregnating cobalt nitrate on the same support. Dispersion dropped after ROR treatment, while synthesis activities increased. Activity increase after ROR treatment was not caused by improved metal dispersion, but by an increase in turnover frequency of the metal sites. In other words, the activity per metal site increased indicating that the ROR treatment has brought the catalyst to its most efficient activity per unit weight of metal.

Activity tests were made after similar reduction and ROR treatments, respectively. An 0.5 gram sample of each catalyst was treated in 5,000 cubic centimeters per gram per hour of flowing hydrogen in the quad unit reactor before each test. The activity tests were made at atmospheric pressure using 1680 cubic centimeters per gram per hour of synthesis gas flow and 195° C. at a hydrogen to carbon monoxide ratio of 1.5. After the test, the catalysts were purged in hydrogen for one hour at 185° C. before they were heated to 350° C. in hydrogen. After the second test, they were again held in hydrogen to strip hydrocarbons, and then purged in nitrogen and cooled to room temperature for the air passivation step.

The results are set forth below in Table III:

TABLE III

| Catalyst | CO Conversion Rate (cc/gram metal/hour) | |
|---|---|---|
| | R350 | ROR |
| A | 1506 | 1726 |
| C | 1009 | 2110 |
| D | 1336 | 1980 |

The ROR activation increased activity of Catalyst C by 109 percent and Catalyst D by 48 percent.

EXAMPLE 3

This example demonstrates the effect of using a silica support rather than an alumina support in connection with the cobalt carbonyl catalyst of the present invention.

A catalyst was prepared in the same manner as "Catalyst C", as described in Example 2, with the exception that a fluid silica (commercially available as Ketjen F5) rather than a fluid alumina support was employed. Samples of this catalyst ("Catalyst E") were subjected to activity tests in the same manner as described in Example 2 for Catalyst C at 195° C. at a hydrogen to carbon monoxide ratio of 1.5 are set forth in Table IV below:

TABLE IV

| Catalyst | CO Conversion Rate (cc/gram metal/hour) | |
|---|---|---|
| | R350 | ROR |
| C | 1009 | 2110 |
| E | 1421 | 2670 |

The results set forth in Table IV show that the use of a silica support provides a higher conversion rate than that achieved with alumina. Higher rates were achieved on silica using ROR. Thus, the conversion rate of Catalyst C was improved by 109 percent, while that of Catalyst E was improved by 88 percent. The $C_{5+}$ selectivity is much improved by the ROR treatment.

EXAMPLE 4

The preparation of the catalysts used in the following experiments is exemplified by the following description of the preparation of the catalyst containing 0.05 weight percent ruthenium. The support was 70 grams of extrudate of a gamma-alumina (Ketjen CK-300 commercially available from Akzo Chemie) which had been ground and sieved to 16-30 mesh size (0.589-1.168 mm) and heated in air at 750° C. for 16 hours. Separate portions comprising 0.1680 gram of ruthenium acetylacetonate, 2.336 grams of lanthanum nitrate, [La(NO$_3$)$_3$ 6H$_2$O], and 87.563 grams of cobalt nitrate, [Co(NO$_3$)$_2$ 6H$_2$O], were dissolved in 181 cubic centimeters of acetone. The solution was divided into three equal parts and the alumina was contacted with the first portion of the catalyst solution with stirring. Solvent was removed from the impregnated alumina in a rotary evaporator at 40° C. The dried material was then calcined in air at 300° C. for two hours. The calcined catalyst was then impregnated with the second portion of the catalyst solution and the drying and calcining steps were repeated. The calcined catalyst was then impregnated, dried, and calcined as before for a third time. The catalyst analyzed 20.00 weight percent cobalt, 1.00 weight percent lanthanum oxide, 0.05 weight percent ruthenium, and the remainder alumina.

A sample of the catalyst (F) is reduced in 4800 cubic centimeters per gram per hour of hydrogen while heating at the rate of 1° C. per minute to a temperature of 350° C. for a period of fifteen hours. A second sample (G) is reduced by passing 4800 cubic centimeters per gram per hour of hydrogen over the catalyst sample while heating at a temperature of 1° C. per minute until a temperature of 350° C. is reached and then that temperature is maintained for fifteen hours. Next, the reduced catalyst is subjected to passivation and then is oxidized in air at 300° C. for sixteen hours. The oxidized catalyst is then reduced once again by flowing 4800 cubic centimeters per gram per hour of hydrogen while heating at the rate of 1° C. per minute until the temperature of 350° C. is reached and then held for fifteen hours.

The foregoing preparation and activation procedures were repeated, with the exception that the ruthenium content was varied to provide catalyst samples containing 0.10, 0.50 and 1.00 weight percent ruthenium.

Meanwhile, for comparative purposes, a catalyst substantially identical to the foregoing catalyst was prepared, with the exception that the ruthenium was omitted. The ruthenium-free catalyst was prepared by utilizing a gamma-alumina extrudate (Ketjen C-300) that had been ground and sieved to 16-40 mesh and calcined at 750° C. An impregnation solution was prepared by dissolving 1.59 grams of lanthanum nitrate, [La(NO$_3$)$_3$ 6H$_2$O], and 59.28 grams of cobalt nitrate, [Co(NO$_3$)$_2$ 6H$_2$O], in 120 cubic centimeters of acetone. The impregnation solution was divided into three equal parts and 47.40 grams of the alumina support was saturated with the first portion of the impregnation solution. The solvent was removed in a rotary evaporator at 40° C., and then calcined in air at 300° C. for two hours. The second portion of impregnation solution is added to the calcined catalyst, evacuated to dryness at 40° C. for one hour and then calcined at 300° C. in air for two hours. The third portion of the catalyst solution is added, and once again, the impregnated catalyst is evacuated to dryness at 40° C. for one hour and calcined at 300° C. in air for two hours. Next, separate samples of the impregnated catalyst are subjected to activation as previously described in connection with the ruthenium-containing catalyst utilizing the type F-G activation treatments.

A series of tests were conducted to evaluate the effect of minute amounts ruthenium as compared with cobalt upon activity of the catalyst in converting synthesis gas to hydrocarbons. In each test, synthesis gas containing 35 weight percent carbon monoxide and 65 weight percent hydrogen were passed over the catalyst sample under a pressure of 1 atmosphere. The catalysts activated using procedures F and G were tested using 1680 cubic centimeters of synthesis gas per gram of catalyst per hour.

The results of the tests are set forth in Table V, below:

TABLE V

| Test No. | Ru (Wt. %) | Co/Ru Ratio (Wt.) | Co/Ru Ratio (Molar) | 195° C. CO Conversion Rate (cc/gram metal/hour) R350 (F) | 195° C. CO Conversion Rate (cc/gram metal/hour) ROR (G) |
|---|---|---|---|---|---|
| 1 | 0.0 | — | — | 382 | 476 |
| 2 | 0.05 | 400 | 693 | 780 | 968 |
| 3 | 0.10 | 200 | 346 | 879 | 1093 |
| 4 | 0.50 | 40 | 69 | 1034 | 1415 |
| 5 | 1.00 | 20 | 35 | 930 | 1286 |

As can be seen from the results in Table V (Test Nos. 2-5), the use of ruthenium significantly improved catalyst activity as compared with those tests in which no ruthenium was present (Test No. 1). Moreover, of particular significance is the fact that even when the Co/Ru molar ratio exceeded 200/1, namely in Tests 2 and 3, the catalyst activity increased in excess of 100 percent over that in which ruthenium was absent.

The ROR activation produced catalysts that were 24-34 percent more active than corresponding catalysts that were reduced just once.

EXAMPLE 5

The following example demonstrates the improved activity of catalysts activated using the procedure of the present invention when prepared by precipitation.

A catalyst is prepared by aqueous precipitation containing 20 weight percent cobalt, 1 weight percent lanthanum oxide with the amount of ruthenium being varied using the procedure described in U.S. Pat. No. 4,088,671 to T. P. Kobylinski, in which 125.8 grams of cobalt nitrate, [Co(NO$_3$)$_2$ 6H$_2$O], 1.32 grams of ruthenium chloride, [RuCl$_3$], and 3.38 grams of lanthanum nitrate, [La(NO$_3$)$_3$ 6H$_2$O] were dissolved in 1300 cubic centimeters of distilled water. A second solution was prepared by dissolving 85.5 grams of K$_2$CO$_3$ in 1300 cubic centimeters of distilled water. The two solutions were separately heated to boiling, and then both solutions were added rapidly with vigorous stirring to 500 cubic centimeters of boiling distilled water, and immediately thereafter 100 grams of 100 mesh gamma-alumina were admixed with stirring and the stirring was continued for 10 minutes. The K$_2$CO$_3$ coprecipitates the metals as carbonates onto the alumina support. The resultant mixture was filtered rapidly and the precipitate was washed with distilled water until there was no evidence of potassium or nitrates remaining. The precipitate was then dried at 120° C. for 16 hours and then calcined at 350° C. for 16 hours in air. The catalyst was divided into separate portions with the first portion (H) being reduced by passing hydrogen over the catalyst at the rate of 840 cubic centimeters per gram per hour while heating at the rate of 1° C. per minute until the catalyst reached 350° C. at which temperature the catalyst is held for six hours. A separate portion of the catalyst (I) is reduced in hydrogen flowing at the rate of 3500 cubic centimeters per gram per hour while being heated to 110° C. at the rate of 10° C. per minute. The catalyst was held at 110° C. for a period of one hour and then heated to 200° C. at the rate of 0.5° C. per minute, held for two hours, and then heated to 350° C. at the rate of 1° C. per minute and held at 350° C. for 10 hours. Next, passivation of the catalyst is conducted in flowing air, and then the catalyst is reduced once again by passing hydrogen at the rate of 840 cubic centimeters per gram per hour while heating at a rate of 1° C. per minute until the temperature of 350° C. is reached and then holding at that temperature for six hours.

The resulting precipitated catalysts were then tested for activity by contact with synthesis gas containing 2 parts carbon monoxide and 3 parts hydrogen on mole basis at a temperature of 195° C. under 1 atmosphere total pressure at a synthesis gas flow rate of 1680 cc/g/h.

The results are set forth below in Table VI:

TABLE VI

| Test No. | Co (Wt. %) | Ru (Wt. %) | Co/Ru Ratio (Wt.) | Co/Ru Ratio (Molar) | CO Conversion Rate (cc/g metal/h) R350 (H) | CO Conversion Rate (cc/g metal/h) ROR (I) |
|---|---|---|---|---|---|---|
| 1 | 20 | 0.0 | — | — | 210 | 318 |
| 2 | 20 | 0.05 | 400 | 693 | 305 | 414 |
| 3 | 20 | 0.15 | 113 | 231 | 382 | 538 |
| 4 | 20 | 0.50 | 40 | 69 | 563 | 936 |
| 5 | 20 | 1.00 | 20 | 69 | 499 | 477 |

The results set forth in Table VI demonstrate that in all but one case the use of the ROR treatment improved catalyst activity. In tests where the amount of ruthenium exceeded about 0.5 weight percent, there was a 4% decline.

EXAMPLE 6

A 20.78 grams portion of Ketjen 000–1:5E gamma alumina was calcined 2 hours at 600° C., then ground and sieved to 20–40 mesh granules. It was impregnated with 12.34 grams of cobalt nitrate hexahydrate plus 3.68 grams of cerium (III) nitrate hexahydrate dissolved in 24 mililiters of distilled water.

The impregnated catalyst was dried for 2 hours at 120° C. and then was heated in a flow of 200 cc/minute of dry air at 1° C./minute to 300° C. and was held at that temperature for 2 hours before being cooled and stored. This catalyst is designated as Catalyst J.

A catalyst was prepared in an identical manner, with the same weights of alumina, cerium nitrate, and water, but with 12.33 grams nickel nitrate hexahydrate in place of cobalt nitrate. This catalyst is designated as Catalyst K.

The catalysts were tested for synthesis gas conversion after activation by procedures F (reduction to 350° C.) or G (ROR treatment of the present invention, which is reduction to 350° C., oxidation to 300° C., and reduction again to 350° C.). Results obtained at 195° C., a hydrogen to carbon monoxide molar ratio of 1.5, and atmospheric pressure are set forth in Table VII below:

TABLE VII

| Catalyst | Wt. % Metal | Wt. % Cerium | CO Conversion Rate (cc/g metal/h) R350 | CO Conversion Rate (cc/g metal/h) ROR |
|---|---|---|---|---|
| J | 10 (Co) | 6 | 650 | 988 |
| K | 10 (Ni) | 6 | 51 | 90 |

The results show that ROR activation also improves the activity of catalysts made by aqueous impregnation, and that it is effective for nickel as well as cobalt.

EXAMPLE 7

Three of the ruthenium-promoted cobalt catalysts described in Example 4 were also tested for ethane hydrogenolysis after activation procedures F (R350) and G (ROR) of Example 4. The conversion to methane were measured at 225° C., a hydrogen to ethane molar ratio of 10, and atmospheric pressure. The results are set forth in Table VIII below:

TABLE VIII

| Test No. | % Co | % Ru | Ethane Conversion Rate (cc/g metal/h) R350 (F) | Ethane Conversion Rate (cc/g metal/h) ROR (G) |
|---|---|---|---|---|
| 1 | 20 | 0.05 | 16.2 | 24.8 |
| 2 | 20 | 0.10 | 18.8 | 29.6 |
| 3 | 20 | 0.50 | 63.3 | 71.2 |

The results in Table VIII show that the ROR activation also improves the catalysts' activity for ethane hydrogenolysis.

What is claimed is:

1. A process for the preparation of a catalyst useful for conversion of synthesis gas to a product containing liquid hydrocarbons, said process comprising:
   (A) depositing cobalt or nickel precursor on a refractory metal oxide support by impregnation or precipitation to distribute cobalt or nickel as crystallites on said support to form a supported catalyst, and
   (B) activating said supported catalyst by subjecting said supported catalyst to the steps, in sequence, of (i) reduction in hydrogen gas, (ii) oxidation in an oxygen-containing gas and (iii) reduction in hydrogen gas, steps (i), (ii) and (iii) being conducted at a temperature of from about 100° to about 450° C. to form an, activated, supported catalyst more active for conversion of synthesis gas after said step (iii) than after step (i).

2. The process of claim 1 wherein said catalyst is prepared by subjecting cobalt on a refractory metal oxide support to said activation procedure.

3. The process of claim 1 wherein said catalyst is prepared by subjecting nickel on a refractory metal oxide support to said activation procedure.

4. The process of claim 1 wherein said support is alumina or silica.

5. The process of claim 4 wherein said support is alumina.

6. The process of claim 1 wherein said first reduction step (i) is conducted at a temperature in the range of from about 200° to about 450° C.

7. The process of claim 6 wherein said oxidation step (ii) is conducted at a temperature in the range of between about 250° and about 400° C.

8. The process of claim 7 wherein said second reduction step (iii) is conducted at a temperature in the range of from about 200° to about 450° C.

9. The process of claim 1 wherein said activation steps are conducted while heating at a rate of from about 0.1° to about 2° C. per minute.

10. The process of claim 1 wherein said catalyst contains from about 5 to about 15 weight percent cobalt.

11. The process of claim 1 wherein said catalyst is prepared by impregnating said support with a non-aqueous, organic impregnating solution of a cobalt salt prior to said activation procedure.

12. The process of claim 11 wherein said non-aqueous, organic impregnation solution additionally contains a ruthenium salt.

13. The process of claim 1 wherein said activation is conducted at a temperature in the range of between about 250° and about 400° C.

14. The process of claim 1 wherein said catalyst additionally contains between about 0.05 and about 0.50 weight percent ruthenium.

15. The process of claim 1 wherein said catalyst consists essentially of cobalt on alumina.

16. The process of claim 1 wherein said catalyst additionally contains a lanthanum or manganese promoter.

17. The process of claim 1 wherein step (i) is conducted in the presence of substantially pure hydrogen.

18. The process of claim 1 wherein step (i) is conducted in the presence of a hydrogen-nitrogen mixture.

19. A catalyst for the conversion of synthesis gas to a product containing liquid hydrocarbons said catalyst prepared by a process comprising:
(A) depositing cobalt or nickel precursor on a refractory metal oxide support by impregnation or precipitation to distribute cobalt or nickel as crystallites on said support to form a supported catalyst, and
(B) activating said supported catalyst by subjecting said supported catalyst to the steps, in sequence, of (i) reduction in hydrogen gas, (ii) oxidation in an oxygen-containing gas and (iii) reduction in hydrogen gas, steps (i), (ii) and (iii) being conducted at a temperature of from about 100° to about 450° C. to form an, activated, supported catalyst more active for conversion of synthesis gas after said step (iii) than after step (i).

20. The catalyst of claim 19 wherein said catalyst is prepared by subjecting cobalt on a refractory metal oxide support to said activation procedure.

21. The catalyst of claim 19 wherein said catalyst is prepared by subjecting nickel on a refractory metal oxide support to said activation procedure.

22. The catalyst of claim 19 wherein said support is alumina or silica.

23. The catalyst of claim 22 wherein said support is alumina.

24. The catalyst of claim 19 wherein said first reduction step (i) is conducted at a temperature in the range of from about 200° to about 450° C.

25. The catalyst of claim 24 wherein said oxidation step (ii) is conducted at a temperature in the range of between about 250° and about 400° C.

26. The catalyst of claim 19 wherein said second reduction step (iii) is conducted at a temperature in the range of from about 200° to about 450° C.

27. The catalyst of claim 19 wherein said activation steps are conducted while heating at a rate of from about 0.1° to about 2° C. per minute.

28. The catalyst of claim 19 wherein said catalyst contains from about 5 to about 15 weight percent cobalt.

29. The catalyst of claim 19 wherein said catalyst is prepared by impregnating said support with a non-aqueous, organic impregnating solution of a cobalt salt prior to said activation procedure.

30. The catalyst of claim 29 wherein said non-aqueous, organic impregnation solution additionally contains a ruthenium salt.

31. The catalyst of claim 29 wherein said non-aqueous solvent is acetone.

32. The catalyst of claim 29 wherein said activation is conducted at a temperature in the range of between about 250° and about 400° C.

33. The catalyst of claim 19 said catalyst additionally contains between about 0.05 and about 0.50 weight percent ruthenium.

34. The catalyst of claim 19 wherein said catalyst consists essentially of cobalt on alumina.

35. The catalyst of claim 19 wherein said support is silica.

36. The catalyst of claim 35 wherein said catalyst additionally contains a lanthanum or manganese promoter.

37. The catalyst of claim 19 wherein step (i) is conducted in the presence of substantially pure hydrogen.

38. The catalyst of claim 19 wherein step (i) is conducted in the presence of a hydrogen-nitrogen mixture.

* * * * *